United States Patent [19]
Hach

[11] 3,953,136
[45] Apr. 27, 1976

[54] METHOD AND APPARATUS FOR AUTOMATICALLY ANALYZING FLUIDS

[75] Inventor: Clifford C. Hach, Ames, Iowa

[73] Assignee: Hach Chemical Company, Ames, Iowa

[22] Filed: Mar. 15, 1974

[21] Appl. No.: 451,472

[52] U.S. Cl. .................. 356/181; 23/230 R; 23/253 R; 250/576; 356/36; 356/184; 356/205; 356/246
[51] Int. Cl.² .......................... G01J 3/50
[58] Field of Search .................. 356/36, 93–97, 356/181, 184, 204–206, 246; 250/576; 23/253 R, 230 R; 350/61

[56] References Cited
UNITED STATES PATENTS

| | | | |
|---|---|---|---|
| 1,960,615 | 5/1934 | Baker | 23/253 R |
| 2,019,871 | 11/1935 | Pettingill et al. | 23/253 R X |
| 3,401,591 | 9/1968 | Anthon | 356/181 X |
| 3,844,661 | 10/1974 | Birkett et al. | 350/61 X |

*Primary Examiner*—John K. Corbin
*Assistant Examiner*—F. L. Evans
*Attorney, Agent, or Firm*—Wolfe, Hubbard, Leydig, Voit & Osann, Ltd.

[57] ABSTRACT

A method of colorimetrically analyzing even heavily turbid or already strongly colored water by first sensing transmitted light from a light beam through a sample of the fluid, adding color-producing test reagents to the sample, again sensing transmitted light from an identical light beam, and comparing the sensed light readings to detect the change, if any, produced by the added reagents. Two colorimetric cells are used, one for testing before the addition of reagents and the other after, with the cells being defined by glass cylinders in which pistons reciprocate to pump measured samples to the cylinders, clean the cylinders on each pumping stroke, and "valve" or block the light beam so that the other cylinder can be "read". Simple displacement pumps for the reagents, and the cell pistons, cooperate with valves defined by pincher arms squeezing flexible tubing to move measured amounts of sample and reagent throughout the analyzer. A common drive simplifies obtaining proper relative operation of the analyzer components.

5 Claims, 9 Drawing Figures

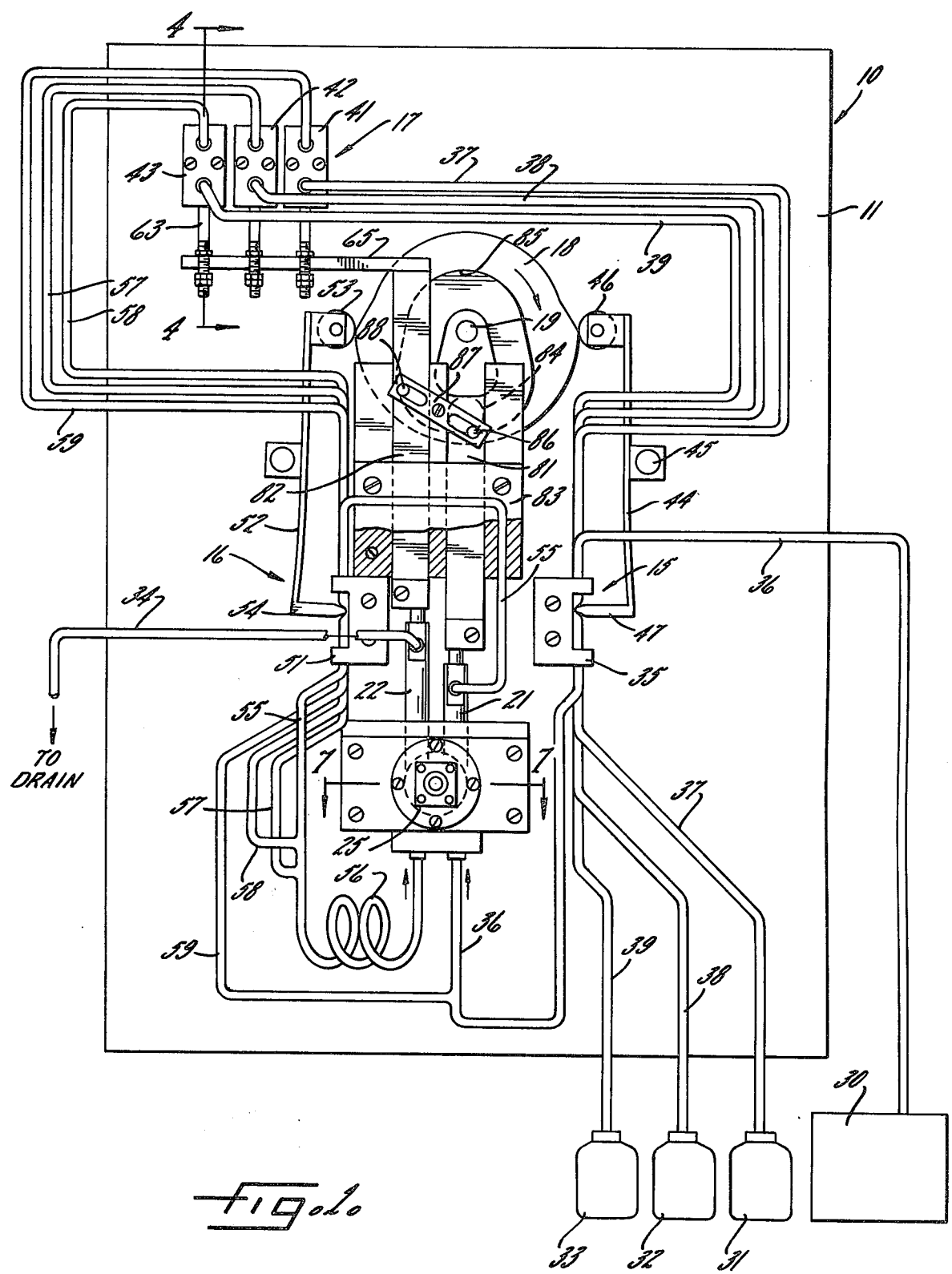

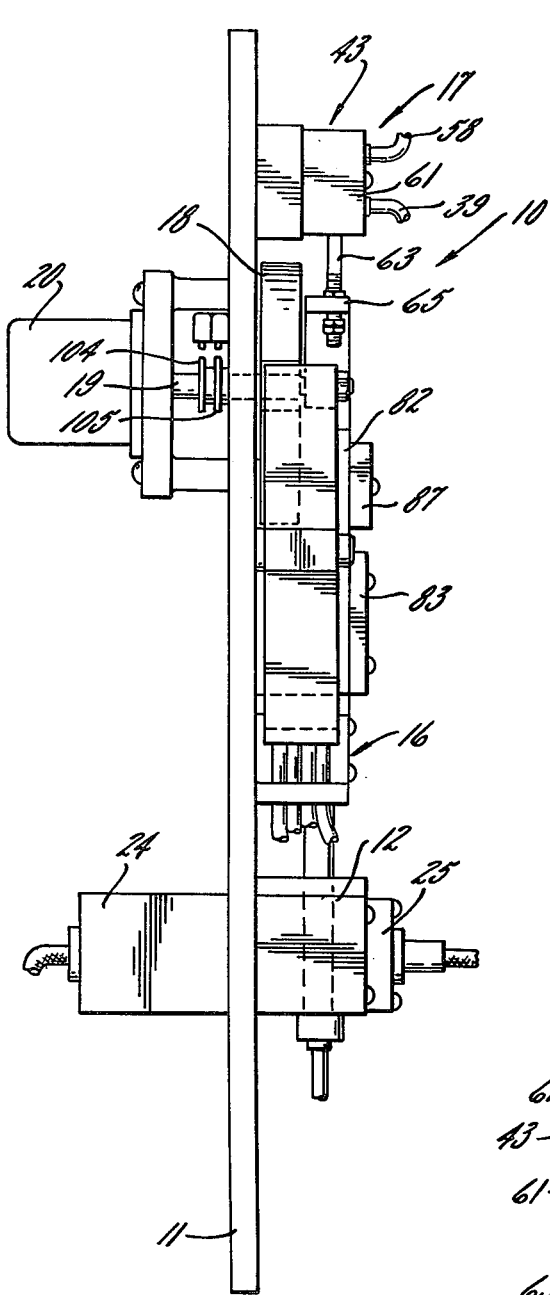
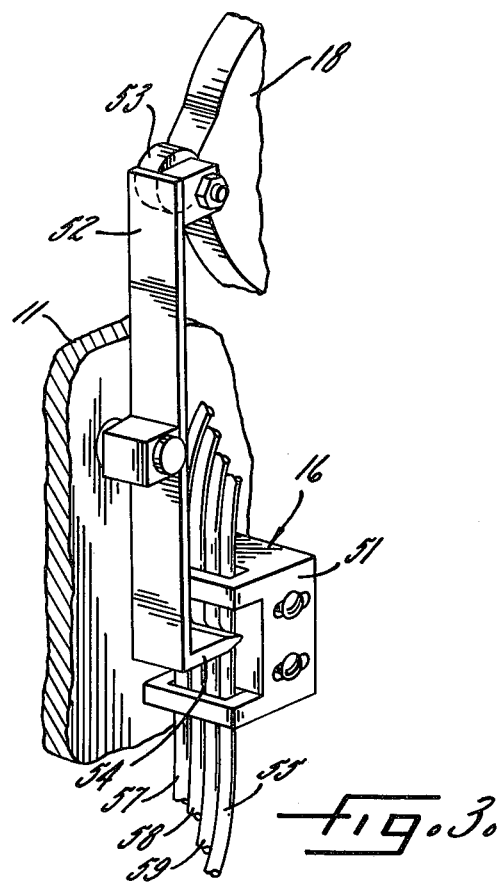
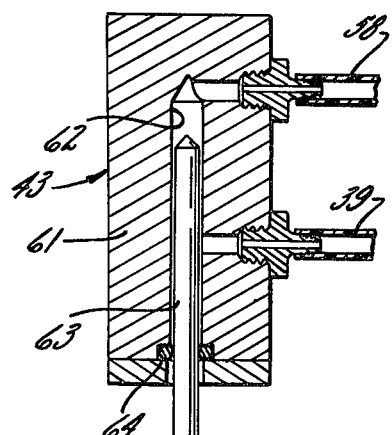
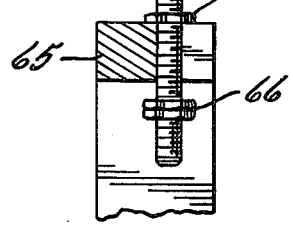

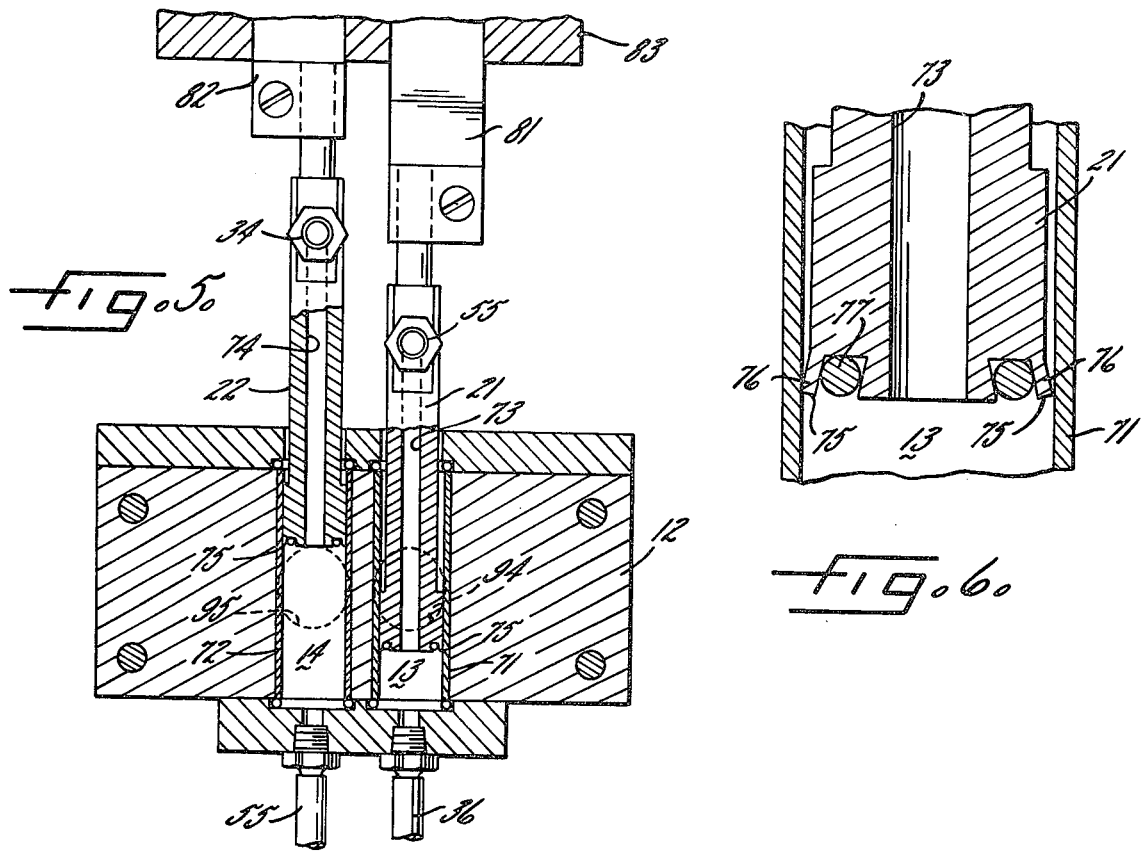
fig. 5
fig. 6
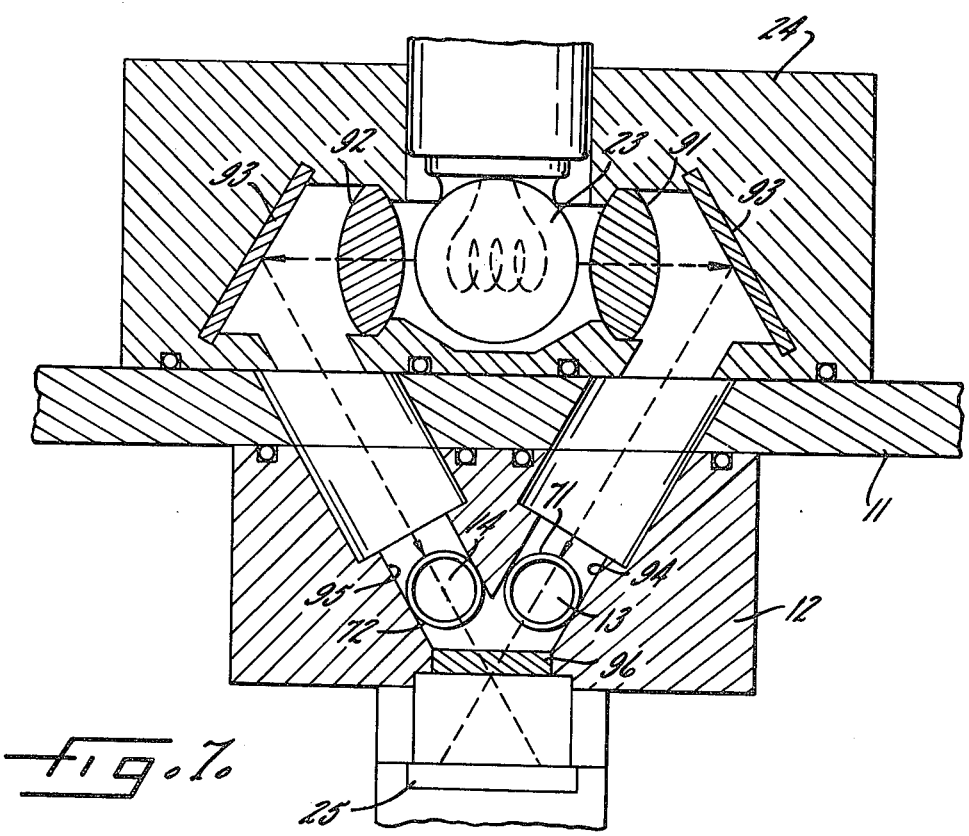
fig. 7

METHOD AND APPARATUS FOR AUTOMATICALLY ANALYZING FLUIDS

This invention relates generally to automatic chemical analyzers and more particularly concerns a continuous fluid analyzer and method for making colorimetric analysis on successive water samples.

Automatic analyzers for monitoring a wide variety of water parameters have long been known to the art and industry. Commonly, such analyzers isolate a water sample of given size, add test reagents of known concentrations and volumes, and then read the color change produced as indicative of the presence and concentration of the substance for which the test is designed. Color changes are efficiently detected by sensing transmitted light filtered to the particular color, or wave length, involved in the given test.

Color change analyzers have been very effective and successful in applications where essentially clean, clear water is under test. Obviously, if the test samples are already colored or are turbid, the sensing light beam is affected by both the turbidity particles and the original or background color so that any color change produced by the test reagents is not accurately measured. Moreover, if "dirty" water is run through an analyzer, it can be expected that the light path for the color-change sensing light will become fouled and, in other cases, distorted by clinging air bubbles.

While not exactly a widespread problem, because automatic analyzers for turbid water are uncommon (if they heretofore existed at all), it is the fact that adding test reagents to a turbid sample could well affect the turbidity of the sample as well as its color, with the result that the sensing light beam would not distinguish between the color change and the turbidity change.

It is the primary aim of the present invention to overcome these problems and provide an automatic colorimetric analyzer that will function effectively, and accurately over long periods of time, in the analysis of even heavily turbid or strongly colored water samples.

It is an object of the invention to provide an analyzer of the above kind which is simple in design so as to be reliable, relatively inexpensive to manufacture, and easy to service and maintain.

Another object is to provide an analyzer as characterized above which is quite flexible in organization so that its components can be arranged and connected to perform a variety of colorimetric tests.

A further object is to provide an analyzer that requires only the most rudimentary installation facilities in that, in most cases, special pumping or piping would not be needed for either samples or reagents.

Other objects and advantages of the invention will become apparent upon reading the following detailed description and upon reference to the drawings, in which:

FIG. 1 is a front elevation, partially diagrammatic, of an analyzer embodying the present invention;

FIG. 2 is a side elevation of the analyzer shown in FIG. 1;

FIG. 3 is an enlarged fragmentary perspective of one of the valve assemblies of the analyzer shown in FIG. 1;

FIG. 4 is an enlarged fragmentary section of one of the pump assemblies employed in the analyzer of FIG. 1;

FIG. 5 is an enlarged fragmentary section of the colorimetric cells utilized in the analyzer of FIG. 1;

FIG. 6 is an enlarged fragmentary section of a portion of the structure shown in FIG. 5;

FIG. 7 is a further enlarged horizontal section of the cells shown in FIG. 5;

Figure 8:
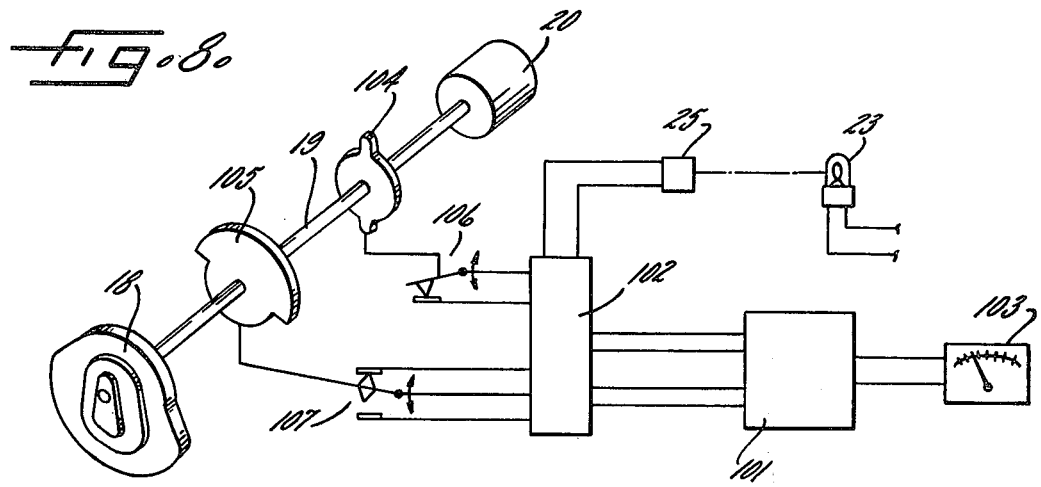
FIG. 8 is a schematic wiring diagram for the analyzer of FIG. 1.

While the invention will be described in connection with a preferred embodiment and procedure, it will be understood that I do not intend to limit the invention to that embodiment or procedure. On the contrary, I intend to cover all alternatives, modifications and equivalents as may be included within the spirit and scope of the invention as defined by the appended claims.

Turning now to the drawings, there is shown in FIG. 1 an analyzer 10 embodying, and intended to perform the method of, the invention. The analyzer 10 includes a mounting plate 11 supporting a housing block 12 containing a reference cell 13 and a test cell 14 (see FIG. 5), an inlet valve assembly 15, an outlet valve assembly 16, a set of reagent pumps 17, and a cam 18 on a shaft 19 journalled in the plate 11 and driven by an electric motor 20. Pistons 21 and 22 reciprocate in the cells 13, 14, respectively, to perform the multiple functions of pumping fluid, cleaning the cells, and timing the transmission of light from a light source 23 mounted in a housing 24 on the rear of the plate 11 to a light sensor 25 mounted on the front of the housing block 12.

It is a feature of the invention that the single cam shaft 19 drives in coordinated fashion the pistons 21, 22, valve assemblies 15, 16, reagent pumps 17 and other moving parts of the analyzer, this drive being mainly through the single cam 18.

To exemplify the invention, the analyzer 10 is set up to and will be described as performing a continuous orthophosphate analysis on samples drawn directly from raw sewage shown schematically contained at 30. The test itself is known, involving straining the sample, preferably filtering out particles above 0.0035 of an inch, adding acid to at least partially dissolve particulate matter, adding a measured amount of ammonium molybdate, next adding a measured amount of amino acid-sulfite, holding the solution for one minute, and then determining the extent of the distinctive blue color change indicative of the phosphate concentration. The analyzer 10 is effective to draw its own stream of samples from the sewage 30 and to pull acid, molybdate and amino acid from reagent bottles 31, 32 and 33, respectively. After testing, the sample stream is discharged through a drain line 34.

Before considering the coordinated functioning of the analyzer 10, it will be helpful to understand the subassemblies. As one aspect of the invention, the inlet valve assembly 15 includes a block 35 guiding and holding four lines of flexible tubing, line 36 running from the sewage 30 to the lower end of the reference cell 13, and lines 37, 38 and 39 running from the respective bottles 31–33 to the respective pumps 41, 42 and 43 in the set 17. The valve operating element is a pinch arm 44 pivoted at 45 on the plate 11 and having a cam follower 46 at one end and a pinch-off bar 47 at the other. When the cam follower 46 rides out on the lobe of the cam 18, as shown in FIG. 1, the bar 47 squeezes all of the tubing lines 36–39 against the block 35 cutting of fluid flow through the lines. Allowing the cam follower 46 to swing counterclockwise on the cam 18 opens the lines of the valve assembly 15. Using 1/16 inch diameter flexible plastic tubing in such an assembly provides a simple, long lasting and reliable multiple valve.

The outlet valve assembly 16 (see FIG. 3) is similar to the assembly 15 having a block 51, a pinch arm 52 with a cam follower 53 and a pinch-off bar 54, and four lines of flexible tubing. A line 55 runs from the top of the reference cell 13, through the valve assembly 16, to a holding loop 56 and then to the lower end of the measuring cell 14. Lines 57 and 58 run from the pumps 42, 43, respectively, and open into and join the line 55 after passing through the valve assembly 16. A fourth line 59 runs from the pump 41 through the assembly 16 to the line 36 going to the bottom of the reference cell. The drain line 34, referred to above, leads from the top of the measuring cell.

The pumps 41–43, constituting another feature of the invention, are identical, and pump 43 (see FIG. 4) includes a housing 61 mounted on the plate 11 and defining a chamber 62 having inlet and outlet passages to which the lines 39 and 58 are respectively connected. A plunger 63 is sized to fit loosely in the chamber 62 and is mounted for reciprocation in a seal 64 preventing leakage from the chamber along the piston. The plunger 63 passes through and is reciprocated by an arm 65 moving up and down through a fixed stroke as described below, and adjustable nuts 66 on the plunger 63 permit the arm-plunger coupling, and thus the volume of fluid pumped per stroke, to be precisely adjusted.

The pumps cooperate with the valve assemblies 15, 16. With the outlet valve assembly 16 holding the line 58 closed, and the inlet valve assembly 15 allowing the line 39 to remain open, downward movement of the plunger 63 caused by downward movement of the arm 65 will draw a fixed quantity of amino acid into the chamber 62. Closing the line 39 and opening the line 58 will, upon upward movement of the plunger 63, pump that same fixed and measured quantity of acid from the chamber 62 and through the line 58. The pumps 41 and 42 are formed and operate similarly, with all the pumps in the set 17 being moved in unison upon upward and downward movement of the arm 65.

In carrying out the invention, the reference and measuring cells 13, 14 include hollow transparent cylinders 71 and 72 in the form of lengths of precision bored glass tubing fixed in the housing block 12, and the pistons 21, 22 are formed with central passages 73 and 74 and lower peripheral edges 75 in wiping engagement with the inner surfaces of the glass tubing 71, 72 (see FIG. 6). Preferably, the pistons 21, 22 are formed of resilient, non-wetting plastic such as Teflon, and have an end groove defining a flexible lip 76 that is resiliently spread by an O-ring 77 so as to create the wiping edges 75 and hold them firmly against the glass cylinders. As already observed, the lines 36, 35 lead to the lower interior ends of the cylinders 71, 72, respectively, and the lines 55 and 34 open into the respective cylinder passages 73, 74.

The pistons 21, 22 are reciprocated by the cam 18 in timed relationship to operation of the valve assemblies 15, 16. Thus, with the outlet valve assembly 16 holding line 55 closed, and the inlet valve assembly leaving line 36 open, upward movement of the piston 21 draws a measured amount of sample into the reference cell 13 through the line 36. In this way the analyzer is capable of pumping its own sample from a considerable distance and thus can be located well above and away from the source of fluid under test. With the line 36 closed and the line 55 open, downward movement of the piston 21 forces the measured sample through the line 55, the valve assembly 16 and to the measuring cell 14.

As observed above, it is a feature of the invention that a common drive facilitates proper coordination of the analyzer's moving parts. The pistons 21, 22 are secured to slide bars 81 and 82, respectively, mounted for vertical movement in a block 83. The slide bar 81 has a cam follower 84 riding in a box cam groove 85 in the cam 18. The bar 81 also carries a pin 86 fitted in a slot in a lever 87 pivoted on the block 83, and the other slide bar 82 carries a corresponding pin 88 engaging another slot in the lever 87. Upward movement of the bar 81 thus rocks the lever 87 counterclockwise to drive the bar 82 downwardly, and vice-versa, so that the pistons 21, 22 move the same distances in opposite directions at the same time.

The bar 82 extends upwardly and carries the arm 65 which drives the set of pumps 17. Also, and as previously described, the periphery of the cam 18 operates the pincher arms 44, 52 of the valve assemblies 15, 16.

In the optical system of the analyzer 10 (see FIG. 7) the single light source 23 directs light through lenses 91 and 92 to mirrors 93 and through passages 94 and 95 to the reference and measuring cells 13, 14. Thus, the same intensity and quality of light is received at each cell. Light transmitted through the cells passes through an appropriately colored filter 96 for the test being utilized to the single common light sensor 25.

The overall method of the invention can now be appreciated. Light of the same intensity and wave length is directed to the two transparent cells 13, 14. The piston 21 moves up drawing a sample into the reference cell 13 and clearing the light passage 94 so that the sensor 25 "sees" a reference value of transmitted light depending on the turbidity and color of the original sample. At this time, the piston 21 is down blocking the light passage 95 to the measuring cell 14. Movement of the pistons in the opposite directions, together with coordinated movement of the valve assemblies 15, 16 and reagent pumps 17, forces the sample from the reference cell 13 toward the measuring cell 14 and adds the reagents through the lines 57, 58 to the sample transmitting line 55.

In the illustrative case, the holding loop 56 gives a detaining period such as one minute for the color producing reaction, successive samples keeping the transmitting lines full, so that, after the holding period, the sample is forced and drawn into the measuring cell 14 upon upward movement of the piston 22. The light transmitted through the measuring cell is then sensed, and by comparing the two light readings, the color change from the test is obtained.

Again referring to the illustrative case, the line 59 and the pump 43 is used to blend a small quantity of acid to the sample in the line 36 before the check of the sample in the reference cell 13. This duplicates the standard test by adding a small amount of acid to the sample prior to using it as a reference sample in standardizing the colorimeter. The effect is to modify the sample before the reference cell check in the same manner as the reagents might effect non-color characteristics between the reference cell and the test cell. That is, the acid will somewhat change the turbidity of the sample prior to the reference cell check so that later addition of the amino acid, which would also affect turbidity, will not produce a turbidity change that would cause a difference in light transmittance. By so preconditioning the sample, any light transmittance changes between the reference cell and the measuring cell can be attributed to the color change of the chemical analysis performed by the analyzer.

Keeping in mind that the samples can be turbid, the continual cleaning of the cell cylinders 71, 72 by the wiping edges 75 of the pistons is obviously an important aspect contributing to the reliable, consistent results obtained from the analyzer 10.

While different kinds of readout arrangements will suggest themselves to those skilled in the art, the analyzer 10 is illustrated associated with a ratio amplifier 101 and a pair of holding amplifiers and logic circuitry 102 so that when no color change is detected by the instrument there is a 100% transmittance reading on a meter 103. In this arrangement, a timing cam 104 and a select cam 105 are mounted on the cam shaft 19 at the rear of the mounting plate 11, each cam operating a switch 106 and 107, respectively, shown schematically in FIG. 8.

The switch 107 selects which of a reference amplifier and a measuring amplifier in the circuitry 102 will receive a signal from the light sensor 25 when the timing switch 106 is closed. When the reference cell 13 is being sensed, the signal from the sensor 25 is directed by the switch 107 to the reference amplifier and is integrated during the period the timing switch 106 is closed. This integrated signal is held for the remainder of the cycle, during which the measuring cell 14 is sensed and that signal directed to a measuring amplifier, the switch 107 being reversed, which is integrated while the timing switch 106 is closed. The ratio amplifier 101 divides the respective signals and, in effect, multiplies by 100 to give a 100% transmittance reading on the meter 103 if the signals are the same as a result of no color change and, in the illustrated case, as a result of no phosphate being present in the sample.

Figure 9:
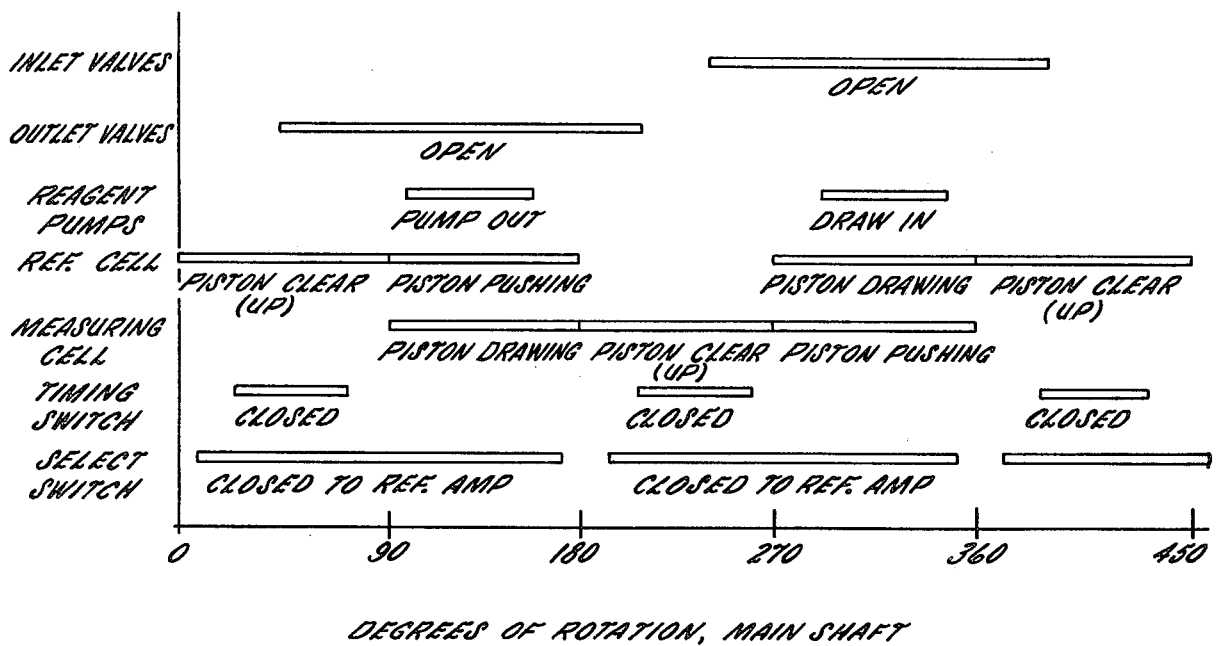
FIG. 9 is a chart showing operating sequences for the parts of the analyzer appearing in FIG. 1.

The sequencing of the timing switch 106 and the select switch 107, as well as the coordinated movements of the other elements of the analyzer 10, will be readily apparent from the timing chart which is FIG. 9.

Because the analyzer 10 performs a colorimetric analysis wherein the color change, if any, is compared against the original sample, the analyzer functions effectively with even heavily turbid and strongly colored samples. Nevertheless, the analyzer, as those skilled in the art will appreciate, is essentially simple in design so as to be reliable, relatively inexpensive to manufacture, and easy to service and maintain. Since the entire mechanism is mounted on a single mounting plate 11, installation in a wall or cabinet can be readily accomplished.

Since the analyzer 10 is self-pumping, little auxiliary or additional equipment is needed for pumping or piping reagents or a sample stream. While the invention has been described in connection with an analyzer set up to perform a given test, it is evident that the components of the analyzer 10 are well suited for arrangement into other configurations so that other colorimetric tests can be formed on a continuous basis from any given sample.

I claim as my invention:

1. In an automatic colorimetric analyzer, the combination of, a housing, a pair of hollow transparent cylinders in said housing, a pair of pistons mounted for reciprocation in respective ones of said cylinders, said housing having light transmitting passages extending to and through said cylinders in regions periodically blocked by said pistons as they reciprocate, said pistons having central passages for transmitting fluid paths, and from said cylinders, said passages being at the top of said cylinders and thus defining air bubble escape path, means including said passages for conveying fluid in a stream from a sample source to first one cylinder and then the other cylinder, valves for selectively blocking said stream between said source and the first cylinder, between said cylinders, and downstream of said second cylinder, a light system including a single lamp and a single photocell for passing and sensing light beams through said cylinders, means for adding a reagent to said sample stream between said cylinders, and means for alternately reciprocating said pistons and operating said valves so as to pump said stream at a uniform measured incremental rate, wipe said cylinders clean, and permit alternate sensing of light beams passing through said cylinders.

2. The combination of claim 1 in which each cylinder is formed of glass tubing with a uniform, cylindrical inner surface, and each piston is formed of a resilient, non-wetting plastic with a groove at one end to define a wiping edge, the combination including means for urging said edge into good wiping engagement with said tubing.

3. The combination of claim 1 in which said valves include lengths of flexible tubing, said valves also including respective pincher arms for squeezing said tubing to block fluid flow and thus close the respective valve, and said last named means being a common drive for reciprocating said piston and alternately actuating said arms to squeeze said tubing.

4. The method of automatically analyzing turbid water colorimetrically comprising the steps of directing two beams of light of the same intensity and wave lengths to respective ones of two transparent cells and toward a light sensor, introducing successive samples of the water under test to one of said cells, directing said samples successively from said one cell to the other cell, adding a test reagent to the sample while it is being directed from said one cell to said other cell, alternately blocking said light beam so as to cause said light sensor to read alternately said beams, comparing said sensor reading so as to detect any difference caused by a color change in the combined sample-reagent, and adding a solution to said water samples before they are introduced to said one cell, said solution having the same effect on turbidity as could later be expected from said reagent.

5. The method of claim 4 in which said cell surfaces in contact with the water are wiped clean each time the light beams are blocked.

* * * * *